United States Patent [19]

Saita et al.

[11] Patent Number: 5,371,238

[45] Date of Patent: Dec. 6, 1994

[54] PROCESS FOR PRODUCING AZACYCLOALKANE DERIVATIVES

[75] Inventors: Masaru Saita, Miyaki; Hisataka Inoue, Kurume; Terumi Hachiya, Kanzaki; Shigenori Yahiro, Kasuya; Kanji Noda, Chikushino, all of Japan

[73] Assignee: Hisamitsu Pharmaceutical Co., Inc., Tosu, Japan

[21] Appl. No.: 50,148

[22] PCT Filed: Oct. 23, 1991

[86] PCT No.: PCT/JP91/01451

§ 371 Date: Apr. 23, 1993

§ 102(e) Date: Apr. 23, 1993

[87] PCT Pub. No.: WO92/07827

PCT Pub. Date: May 14, 1992

[30] Foreign Application Priority Data

Oct. 31, 1990 [JP] Japan ................. 2-291876

[51] Int. Cl.$^5$ ................. C07D 207/26; C07D 211/74; C07D 223; C07D 10

[52] U.S. Cl. ................. 548/551; 546/243; 540/485

[58] Field of Search ................. 548/543, 551; 546/243; 540/485

[56] References Cited

U.S. PATENT DOCUMENTS 4,882,359  11/1989  Nakagawa et al. ................. 514/947

*Primary Examiner*—David B. Springer
*Attorney, Agent, or Firm*—Bucknam and Archer

[57] ABSTRACT

A process for producing an azacycloalkane derivative represented by the following general formula (II):

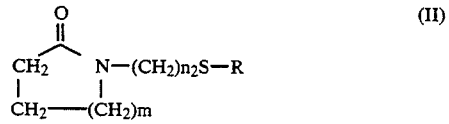

(II)

wherein m is an integer of from 1 to 3, $n_2$ is an integer of from 2 to 10, and R represents an alkyl group having 3 to 12 carbon atoms, characterized by reacting a 1-(n-alkenyl)-azacycloalkan-2-one represented by the following general formula (I):

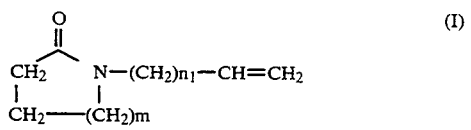

(I)

wherein m is an integer of from 1 to 3, and $n_1$ is an integer of from 0 to 8, with an alkyl mercaptan in the presence of a radical initiator in an organic solvent, treating the reaction mixture thus obtained with a reducing agent in a water-containing organic solvent, and then purifying the treated mixture by distillation.

10 Claims, No Drawings

PROCESS FOR PRODUCING AZACYCLOALKANE DERIVATIVES

TECHNICAL FIELD

The present invention relates to a process For producing an azacycloalkane derivative which is useful in the fields of medicines and agricultural chemicals as a compound having an action of promoting absorption.

BACKGROUND ART

Azacycloalkane derivatives are compounds which are useful as absorption promoters capable of enhancing the penetrability and permeability of drugs while scarcely irritating biomembranes and having little systemic toxicity. Among these compounds, 1-[2-(decylthio)ethyl]azacyclopentan-2-one exerts remarkable effects and, therefore, is expected as highly useful in medicines and agricultural chemicals.

As will be described hereinafter, however, the existing process for producing 1-[2-(decylthio)ethyl]azacyclopentan-2-one with such a high purity as to be applicable to medicines and agricultural chemicals are far from satisfactory from the industrial and economic viewpoints. Therefore, it has been urgently required to develop a process for readily producing such compound at a low cost.

More specifically, the existing processes for producing azacycloalkane derivatives include the following ones, as described in Japanese Patent Application Laid-Open Gazette No. Sho. 62-238261 (238261/1987):

(1) a process comprising reacting an azacycloalkan-2-one with a dihalogenoalkyl in excess in the presence of an alkali metal hydride catalyst to obtain a reaction product and then reacting the product with a halogenoalkyl in the presence of a phase transfer catalyst in an alkaline aqueous solution of sodium sulfide;

(2) a process comprising adding a dihalogenoalkyl in large excess to an azacycloalkan-2-one in the presence of an alkali metal hydride catalyst to obtain a reaction product and then reacting the product with an alkyl mercaptan in the presence of a dehydrohalogenating agent in an inert solvent which does not participate in the reaction;

(3) a process comprising reacting a 1-(n-alkenyl)azacycloalkan-2-one with an alkyl mercaptan in the presence of a radical initiator in benzene or the like;

(4) a process comprising reacting an alkyl mercaptan with a dihalogenoalkyl in excess in the presence of a dehydrohalogenating agent to obtain a reaction product and then reacting the product with an azacycloalkan-2-one; and (5) a process comprising adding a halogenoalkyl mercaptan to an alkali salt of an azacycloalkan-2-one to obtain a reaction product and then reacting the product with a halogenoalkyl in the presence of a dehydrohalogenating agent.

However, each of these processes has some serious industrial problems and, therefore, is not satisfactory. In the above processes (1), (2), (4) and (5), for example, it is necessary to use an alkali metal hydride which is expensive and difficult to handle. In addition, the reaction time is as long as about 12 hours and a product with a high purity can be hardly obtained. Therefore, much labor is required for purifying the product. Thus, these processes cannot be regarded as industrially advantageous ones. Furthermore, it requires a long time and a large cost to secure a high purity by these processes.

On the other hand, the above process (3) is a relatively easy one. However, a considerably large amount of dialkyl disulfides having boiling points closely similar to those of azacycloalkane derivatives are formed as by-products in this case. Accordingly, a product of such a high purity as to be applicable to medicines and agricultural chemicals can be hardly obtained by simple procedures such as distillation (see Comparative Example 1 which will be given hereinafter). In order to remove these by-products, it is necessary to perform troublesome operations such as column chromatography or recrystallization prior to distillation. Thus, this process cannot be regarded as an economically advantageous one. Further, it has been confirmed that the use of benzene or the like as the reaction solvent causes the formation of isomers which lowers the purity of the product, since it is impossible to completely remove these isomers by column chromatography, recrystallization or distillation.

An object of the present invention is to solve these problems encountered in the prior art and more particularly it is to provide an industrially advantageous process for producing an azacycloalkane derivative whereby the desired compound with a high purity can be easily obtained and good economical and operation characteristics can be achieved.

Disclosure of the Invention

The present inventors have conducted intensive studies in order to solve the above problems and, as the result of their studies, found that an azacycloalkane derivative with a high purity can be obtained through distillation without resort to, for example, column chromatography by performing a radical reaction between a 1-(n-alkenyl)azacycloalkan-2-one and an alkyl mercaptan and converting the dialkyl disulfides thus formed as the by-products into alkyl mercaptans by reaction with a reducing agent. The present invention is based on this finding.

The present invention is a process for producing an azacycloalkane derivative represented by the following general formula (II):

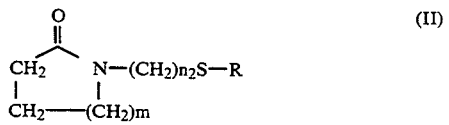

wherein m is an integer of from 1 to 3,
$n_2$ is an integer of from 2 to 10, and
R represents an alkyl group having 3 to 12 carbon atoms,
characterized by reacting a 1-(n-alkenyl)azacycloalkan-2-one represented by the following general formula (I):

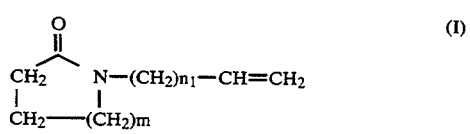

wherein m is an integer of from 1 to 3, and $n_1$ is an integer of from 0 to 8,
with an alkyl mercaptan in the presence of a radical initiator in an organic solvent, treating the reaction mixture thus obtained with a reducing agent in a water-containing organic solvent, and then purifying the treated mixture by distillation.

In the present invention, the 1-(n-alkenyl)azacycloalkan-2-one represented by the above general formula (I) is reacted with an alkyl mercaptan in the presence of a radical initiator in an organic solvent.

The 1-(n-alkenyl)azacycloalkan-2-ones which can be used for the present invention are exemplified by 1-vinyl-2-pyrrolidone, 1-allyl-2-pyrrolidone, 1-butenyl-2-pyrrolidone, 1-pentenyl-2-pyrrolidone, 1-hexenyl-2-pyrrolidone, 1-heptenyl-2-pyrrolidone, 1-octenyl-2-pyrrolidone, 1-vinylazacyclohexan-2-one, 1-propenylazacyclohexan-2-one, 1-butenylazacyclohexan-2-one, 1-vinylazacyclopentan-2-one, 1-allylazacycloheptan-2-one and 1-butenylazacycloheptan-2-one.

The alkyl mercaptans are exemplified by linear and branched ones such as propyl mercaptan, butyl mercaptan, pentyl mercaptan, hexyl mercaptan, heptyl mercaptan, octyl mercaptan, nonyl mercaptan, decyl mercaptan and dodecyl mercaptan.

The molar ratio of the alkyl mercaptan to the 1-(n-alkenyl)azacycloalkan-2-one may range from 0.8 to 2.0, preferably from 0.9 to 1.1, namely, allowing a nearly equimolar reaction.

The radical initiators which can be used for the present invention are exemplified by benzoyl peroxide, acetyl peroxide, tert-butyl peroxide, cumene hydroperoxide, 4-bromobenzenediazonium hydroxide, triphenylmethylazobenzene, N-nitrosoacylanilide, 2,2'-azobisisobutyronitrile, tetraphenylsuccinonitrile and hydrogen peroxide, among which benzoyl peroxide and 2,2'-azobisisobutyronitrile are preferable.

The organic solvents are exemplified by benzene, toluene, xylene, methanol, ethanol, 1-propanol, 2-propanol, cyclohexane, acetonitrile, ethyl acetate, acetic acid, tetrahydrofuran, dioxane and N,N-dimethylformamide. It is preferable to use an alcohol, still preferably ethanol or propanol, therefor. When an alcohol is used as the organic solvent, the Formation of by-products other than dialkyl disulfides, i.e., isomers formed by the radical reaction can be suppressed. Thus, the treatment with a reducing agent, as will be described hereinbelow, can achieve relatively good results.

The radical reaction is conducted at a temperature of from 50° to 150° C., preferably from 70° to 120° C., for about 0.5 to 20 hours, preferably for 1 to 5 hours.

In the present invention, the reaction mixture thus obtained is reacted with a reducing agent in a water-containing organic solvent and further purified by distillation.

The reducing agents which can be used for the present invention are exemplified by metal sulfides such as sodium hydrogensulfide and sodium sulfide; metals such as tin and zinc with acids; trialkylphosphines such as trimethylphosphine, triethylphosphine, tripropylphosphine and tributylphosphine; thiols; triphenylphosphine and sodium arsenate, among which trialkylphosphines are preferable and tributylphosphine is still preferable.

The reducing agent is used in an amount of from 0.1 to 50% by mole, preferably from 1 to 15% by mole, based on the 1-(n-alkenyl)azacycloalkan-2-one.

The water-containing organic solvent which can be used in the reduction treatment are exemplified by methanol, ethanol, 1-propanol, 2-propanol, acetonitrile, acetic acid, tetrahydrofuran and N,N-dimethylformamide, among which alcohols are preferable. The water content of the water-containing organic solvent may range from 3 to 50%, preferably from 10 to 30%.

The reduction treatment is conducted at a temperature of 300° C. or below, preferably from 0° to 100° C. and still preferably at room temperature (10° to 40° C.). The treatment time ranges from about 0.5 to 5 hours, preferably from 0.5 to 1.5 hours.

In the present invention, the conditions for the radical reaction closely relate to the conditions for the reduction treatment. It is, therefore, necessary to design consistent production conditions. When an alkyl mercaptan is used In molar excess in order to complete the reaction, for example, the amount of the reducing agent required in the reduction treatment is elevated with an increase in the amount of the alkyl mercaptan. When the 1-(n-alkenyl)azacycloalkan-2-one is used in molar excess in order to minimize the formation of dialkyl disulfides, the treatment with the reducing agent is also necessary and the amount of the reducing agent can be reduced correspondingly.

In the present invention, the amount of the reducing agent required should vary as the molar ratio of the 1-(n-alkenyl)azacycloalkan-2-one to the alkyl mercaptan changes. There is the optimum level of the amount of the reducing agent and the use of the reducing agent in an amount exceeding the optimum level causes an economic disadvantage. When the amount of the reducing agent is below the optimum level, on the other hand, the dialkyl disulfides cannot be completely removed. Thus, in the present invention, the reaction conditions and the treatment conditions closely relate to each other so as to exhibit the effects.

The azacycloalkane derivative obtained by the above process scarcely contains any dialkyl disulfide as a by-product. Therefore, the desired compound with a high purity can be very easily obtained through a simple distillation operation.

BEST MODE FOR CARRYING OUT THE INVENTION

To further illustrate the present invention in greater detail, the following Examples and Comparative Examples will be given, but the present invention is not restricted to the embodiments described in these Examples.

Example 1

55.6 g (0.5 mol) of 2-vinylpyrrolidone, 87.2 g (0.5 mol) of n-decyl mercaptan, 0.4 g of 2,2'-azobisisobutyronitrile and 500 ml of ethanol, were introduced in a 1-l reactor and then refluxed under heat for 2 hours.

After allowing the reaction mixture to cool to room temperature, 50 ml of water and 1.8 g of tributylphosphine were added thereto and The obtained mixture was stirred at room temperature for 1 hour. Next, the reaction mixture was incorporated with 500 ml of ethyl acetate, washed with water, dried and then freed from the solvent under a reduced pressure. The oily product thus obtained was distilled to thereby give 87.2 g of 1-[2-(decylthio)ethyl]azacyclopentan-2-one.

The purity of the obtained product determined based on the percentage of the area in gas chromatography was 99.4% and no didecyl disulfide was detected.

The form, column temperature and elemental analysis data of this product were as follows.

The column temperature was measured with a rotary glass tube oven GTO-250 R (mfd. by Shibata Kagaku Kikai Kogyo Co., Ltd.).

Form: colorless, transparent oil, Column temperature: 130°–134° C./0.2 mmHg, Elemental analysis ($C_{16}H_{31}NOS$) calcd.: C: 67.31, H: 10.94, N:4.91, found: C: 67.19, H: 10.84, N:4.87.

Example 2

11.1 g (0.1 mol) of 2-vinylpyrrolidone, 17.4 g (0.1 mol) of n-decyl mercaptan, 0.1 g of benzoyl peroxide and 100 ml of benzene were introduced in a 300-l reactor and then refluxed under heat for 3 hours.

After removing insoluble matters from the reaction mixture by filtering, the filtrate was freed from the solvent under a reduced pressure, 100 ml of methanol, was added 20 ml of water and 0.45 g of tributylphosphine and then stirred at room temperature for 40 minutes. Next, to the reaction mixture was added 100 ml of ethyl acetate, washed with water, dried and then concentrated under a reduced pressure. The oily product thus obtained was distilled to thereby give 18.7 g of 1-[2-(decylthio)ethyl]azacyclopentan-2-one.

The purity of the obtained product determined based on the percentage of the area in gas chromatography was 99.34% and no didecyl disulfide was detected.

The form, column temperature and elemental analysis data of this product determined by the same methods as those described in the above Example 1 were as follows.

Form: colorless, transparent oil, Column temperature: 130°–135° C./0.2 mmHg, Elemental analysis ($C_{16}H_{31}NOS$) calcd.: C: 67.31, H: 10.94, N: 4.91, Found: C: 67.43, H: 11.03, N: 4.86.

Example 3

11.1 g (0.1 mol) of 2-vinylpyrrolidone, 17.4 g (0.1 mol) of n-decyl mercaptan. 0.08 g of 2,2'-azobisisobutyronitrile and 100 ml of toluene were introduced in a 300-l reactor and then refluxed under heat for 2 hours.

The reaction mixture was washed with water, dried, freed from the solvent under a reduced pressure, 200 ml of methanol, 100 ml of water and 4.3 g of sodium sulfide were added and then stirred at room temperature for 2 hours. Next, the reaction mixture was freed from the solvent under a reduced pressure, 100 ml of ethyl acetate, was added washed with water, dried and then concentrated under a reduced pressure. The oily product thus obtained was distilled to thereby give 17.3 g of 1-[2-(decylthio)ethyl]azacyclopentan-2-one.

The purity of the obtained product determined based on the percentage of the area in gas chromatography was 99.1% and no didecyl disulfide was detected.

The form, column temperature and elemental analysis data of this product determined by the same methods as those described in the above Example 1 were as follows.

Form: colorless, transparent oil, Column temperature: 130°–135° C./0.2 mmHg, Elemental analysis ($C_{16}H_{31}NOS$) calcd.: C: 67.31, H: 10.94, N: 4.91, found: C: 67.23, H: 10.86, N: 4.90.

Example 4

55.6 g (0.5 mol) of 2-vinylpyrrolidone, 87.2 g (0.5 mol) of n-decyl mercaptan, 0.4 g of 2,2'-azobisisobutyronitrile and 250 ml of 2-propanol were introduced in a 1-l reactor and then refluxed under heat for 2 hours.

To the reaction mixture was incorporated with 50 ml of water and 1.8 g of tributylphosphine were added and then the mixture was stirred at room temperature for 1 hour. Next, to the reaction mixture was added 250 ml of ethyl acetate, washed with water, dried and then freed from the solvent under a reduced pressure. The oily product thus obtained was distilled to thereby give 90.1 g of 1-[2-(decylthio)ethyl]azacyclopentan-2-one.

The purity of the obtained product determined based on the percentage of the area in gas chromatography was 99.4% and no didecyl disulfide was detected.

The form, column temperature and elemental analysis data of this product determined by the same methods as those described in the above Example 1 were as follows.

Form: colorless, transparent oil, Column temperature: 130°–134° C./0.2 mmHg, Elemental analysis ($C_{16}H_{31}NOS$) calcd.: C: 67.31, H: 10.94, N: 4.91, found: C: 67.19, H: 10.77, N: 4.95.

Example 5

55.6 g (0.5 mol) of 2-vinylpyrrolidone, 78.5 g (0.45 mol) of n-decyl mercaptan, 0.4 g of 2,2'-azobisisobutyronitrile and 300 ml of acetonitrile were introduced in a 1-l reactor and then refluxed under heat for 2 hours.

To the reaction mixture 300 ml of ethanol, 100 ml of water and 15.0 g of sodium sulfide were added the mixture was and then stirred at 60° C. for 30 minutes. Next, the reaction mixture was freed from the solvent under a reduced pressure, 300 ml of ethyl acetate, was added washed with water, dried and then concentrated under a reduced pressure. The oily product thus obtained was distilled to thereby give 81.3 g of 1-[2-(decylthio)ethyl]azacyclopentan-2-one.

The purity of the obtained product determined based on the percentage of the area in gas chromatography was 99.5% and no didecyl disulfide was detected.

The form, column temperature and elemental analysis data of this product determined by the same methods as those described in the above Example 1 were as follows:

Form: colorless, transparent oil, Column temperature: 130°–135° C./0.2 mmHg, Elemental analysis ($C_{16}H_{31}NOS$) calcd.: C: 67.31, H: 10.94, N: 4.91, found: C: 67.27, H: 11.12, N: 4.84.

Example 6

11.1 g (0.1 mol) of 2-vinylpyrrolidone, 17.4 g (0.1 mol) of n-decyl mercaptan, 0.1 g of 2,2'-azobisisobutyronitrile and 100 ml of ethyl acetate were introduced in a 300-ml reactor and then refluxed under heat for 2 hours.

The reaction mixture was washed with water, dried, concentrated under a reduced pressure, 50 ml of methanol, 10 ml of water and 0.45 g of tributylphosphine were added and then the mixture was stirred at room temperature for 1 hour. Next, to the reaction mixture 50 ml of ethyl acetate, was added the mixture washed with water, dried and then freed from the solvent under a reduced pressure. The oily product thus obtained was distilled to thereby give 17.4 g of 1-[2-(decylthio)ethyl]azacyclopentan-2-one.

The purity of the obtained product determined based on the percentage of the area in gas chromatography was 99.5 % and no didecyl disulfide was detected.

The form, column temperature and elemental analysis data of this product determined by the same methods as those described in the above Example 1 were as follows.

Form: colorless, transparent oil, Column temperature: 130°–135° C./0.2 mmHg, Elemental analysis ($C_{16}H_{32}NOS$) calcd.: C: 67.81, H: 10.94, N: 4.91, found: C: 67.89, H: 10.98, N: 4.78.

Example 7

11.1 g (0.1 mol) of 2-vinylpyrrolidone, 17.4 g (0.1 mol) of n-decyl mercaptan, 0.1 g of 2,2'-azobisisobutyronitrile and 50 ml of acetic acid were introduced in a 300-ml reactor and then stirred at 90° C. for 2 hours.

The reaction mixture was treated with 0.29 g of zinc powder and then stirred under heat for 4 hours. Next, to the reaction mixture 300 ml of ethyl acetate, was added and mixture was freed from the insoluble matters by filtering, washed with water, dried and then freed from the solvent under a reduced pressure. The oily product thus obtained was distilled to thereby give 15.9 g of 1-[2-(decylthio)ethyl]azacyclopentan-2-one.

The purity of the obtained product determined based on the percentage of the area in gas chromatography was 99.0% and no didecyl disulfide was detected.

The form, column temperature and elemental analysis data of this product determined by the same methods as those described in the above Example 1 were as follows.

Form: colorless, transparent oil, Column temperature: 130°–134° C./0.2 mmHg, Elemental analysis ($C_{16}H_{31}NOS$) calcd.: C: 67.31, H: 10.94, N: 4.91, found: C: 67.10, H: 10.81, N: 4.79.

Example 8

55.6 g (0.5 mol) of 2-vinylpyrrolidone, 87.2 g (0.5 mol) of n-decyl mercaptan, 0.4 g of 2,2'-azobisisobutyronitrile and 250 ml of ethanol were introduced in a 1-l reactor and then refluxed under heat for 2 hours.

After allowing the reaction mixture to cool to room temperature, 125 ml of water and 21.4 g of sodium sulfide were added and the obtained mixture was stirred at room temperature for 2 hours. Next, 300 ml of ethyl acetate, was added, the mixture washed with water, dried and then freed from the solvent under a reduced pressure. The oily product thus obtained was distilled to thereby give 78.3 g of 1-[2-(decylthio)ethyl]azacyclopentan-2-one.

The purity of the obtained product determined based on the percentage of the area in gas chromatography was 99.3% and no didecyl disulfide was detected.

The form, column temperature and elemental analysis data of this product determined by the same methods as those described in the above Example 1 were as follows.

Form: colorless, transparent oil, Column temperature: 131°–135° C./0.2 mmHg, Elemental analysis ($C_{16}H_{31}NOS$) calcd.: C: 67.31, H: 10.94, N: 4.91, found: C: 67.30, It: 11.20, N: 4.87.

Example 9

55.6 g (0.5 mol) of 2-vinylpyrrolidone, 104.6 g (0.6 mol) of n-decyl mercaptan, 0.4 g of 2,2'-azobisisobutyronitrile and 500 ml of ethanol were introduced in a 1-l reactor and then refluxed for 2 hours.

After allowing the reaction mixture to cool to room temperature, 50 ml of water and 3.1 g of tributylphosphine were added and the obtained mixture was stirred at room temperature for 1 hour. Next, 500 ml of ethyl acetate, was wadded, the mixture washed with water, dried and then freed from the solvent under a reduced pressure. The oily product thus obtained was distilled to thereby give 84.1 g of 1-[2-(decylthio)ethyl]azacyclopentan-2-one.

The purity of the obtained product determined based on the percentage of the area in gas chromatography was 99.3% and no didecyl disulfide was detected.

The form, column temperature and elemental analysis data of this product determined by the same methods as those described in the above Example 1 were as follows.

Form: colorless transparent oil, Column temperature: 130°–135° C./0.2 mmHg, Elemental analysis ($C_{16}H_{31}NOS$) calcd.: C: 67.31, H: 10.94, N: 4.91, found: C: 67.21, H: 10.85, N: 4.88.

Example 10

69.5 g (0.5 mol) of 1-(3-butenyl)azacyclopentan-2-one, 73.0 g (0.5 mol) of n-octyl mercaptan, 0.4 g of 2,2'-azobisisobutyronitrile and 500 ml of ethanol were introduced in a 1-l reactor and then refluxed under heat for 2 hours.

After allowing the reaction mixture to cool to room temperature, 50 ml of water and 1.7 g of tributylphosphine were added thereto and the obtained mixture was stirred at room temperature for 1 hour.

Next, 500 ml of ethyl acetate, was added, the mixture washed with water, dried and then freed from the solvent under a reduced pressure. The oily product thus obtained was distilled to thereby give 82.3 g of 1-[4-(octylthio)butyl]azacyclopentan-2-one.

The purity of the obtained product determined based on the percentage of the area in gas chromatography was 99.6% and no dioctyl disulfide was detected.

The form, column temperature and elemental analysis data of this product determined by the same methods as those described in the above Example 1 were as follows.

Form: colorless, transparent oil, Column temperature: 130°–134° C./0.2 mmHg, Elemental analysis ($C_{16}H_{31}NOS$) calcd.: C: 67.31, H: 10.94, N: 4.91, found: C: 67.06, H: 10.69, N: 4.87.

Example 11

69.5 g (0.5 mol) of 1-(2-propenyl)azacyclohexan-2-one, 80 g (0.5 mol) of n-nonyl mercaptan. 0.4 g of 2,2'-azobisisobutyronitrile and 500 ml of ethanol were introduced in a 1-l reactor and then refluxed under heat for 2 hours.

After allowing the reaction mixture to cool to room temperature, 50 ml of water and 1.7 g of tributylphosphine were added and the obtained mixture was stirred at room temperature for 1 hour. Next, 500 ml of ethyl acetate, was added, the mixture washed with water, dried and then freed from the solvent under a reduced pressure. The oily product thus obtained was distilled to thereby give 88.9 g of 1-[3-(nonylthio)propyl]azacyclohexan-2one.

The purity of the obtained product determined based on the percentage of the area in gas chromatography was 99.14% and no dodecyl disulfide was detected.

The form column temperature and elemental analysis data of this product determined by the same methods as those described in the above Example 1 were as follows.

Form: colorless, transparent oil, Column temperature: 138°–143° C./0.2 mmHg, Elemental analysis ($C_{17}H_{33}NOS$) calcd.: C: 68.17, H: 11.10, N: 4.68, found: C: 67.95, H: 11.01, N: 4.63.

Example 12

83.5 g (0.5 mol) of 1-(3-butenyl)azacycloheptan-2-one, 59.1 g (0.5 mol) of n-hexyl mercaptan, 0.4 g of 2,2'-azobisisobutyronitrile and 500 ml of ethanol were introduced in a 1-l reactor and then refluxed under heat for 2 hours.

After allowing the reaction mixture to cool to room temperature, 50 ml of water and 1.8 g of tributylphosphine were added thereto and the obtained mixture was stirred at room temperature for 1 hour. Next, 500 ml of ethyl acetate, wash added, the mixture washed with water, dried and then freed from the solvent under a reduced pressure. The oily product thus obtained was distilled to thereby give 86.9 g of 1-[4-(hexylthio)butyl-]azacycloheptan-2-one.

The purity of the obtained product determined based on the percentage of the area in gas chromatography was 99.4% and no dihexyl disulfide was detected.

The form, column temperature and elemental analysis data of this product determined by the same methods as those described in the above Example 1 were as follows.

Form: colorless, transparent oil, Column temperature: 134°–139° C./0.2 mmHg, Elemental analysis ($C_{16}H_{31}NOS$) calcd.: C: 67.31, H: 10.94, N: 4.91, found: C: 67.06, H: 10.81, N: 4.81.

Examples 13–56

In accordance with the production process of the above Example 1, various azacycloalkane derivatives represented by the above general formula (II) were obtained.

Table 1 summarizes the azacycloalkane derivative obtained in each of the Examples 13–56, namely, the values of m and $n_2$ and the structure of R in the general formula (II) and the column temperature thereof.

TABLE 1

| Ex. No. | m | $n_2$ | R | Column temp. (°C./mmHg) |
|---|---|---|---|---|
| Ex. 13 | 1 | 2 | S—$(CH_2)_5$—$CH_3$ | 111~117/0.5 |
| Ex. 14 | 1 | 2 | S—$(CH_2)_7$—$CH_3$ | 117~122/0.2 |
| Ex. 15 | 1 | 2 | S—$(CH_2)_{10}$—$CH_3$ | 142~148/0.4 |
| Ex. 16 | 1 | 3 | S—$(CH_2)_7$—$CH_3$ | 122~128/0.2 |
| Ex. 17 | 1 | 3 | S—$(CH_2)_8$—$CH_3$ | 128~132/0.2 |
| Ex. 18 | 1 | 3 | S—$(CH_2)_9$—$CH_3$ | 134~139/0.2 |
| Ex. 19 | 1 | 4 | S—$(CH_2)_6$—$CH_3$ | 125~131/0.2 |
| Ex. 20 | 1 | 5 | S—$(CH_2)_5$—$CH_3$ | 124~129/0.2 |
| Ex. 21 | 1 | 5 | S—$(CH_2)_6$—$CH_3$ | 129~134/0.2 |
| Ex. 22 | 1 | 5 | S—$(CH_2)_9$—$CH_3$ | 155~160/0.5 |
| Ex. 23 | 1 | 6 | S—$(CH_2)_4$—$CH_3$ | 126~131/0.2 |
| Ex. 24 | 1 | 6 | S—$(CH_2)_5$—$CH_3$ | 129~133/0.2 |
| Ex. 25 | 1 | 6 | S—$CH_2$—CH($CH_2CH_3$)($CH_2CH_2CH_2CH_3$) | 144~149/0.2 |
| Ex. 26 | 1 | 7 | S—$(CH_2)_9$—$CH_3$ | 175~181/0.5 |
| Ex. 27 | 1 | 8 | S—$(CH_2)_2$—$CH_3$ | 144~150/0.8 |
| Ex. 28 | 2 | 3 | S—$(CH_2)_9$—$CH_3$ | 143~149/0.2 |
| Ex. 29 | 3 | 3 | S—$(CH_2)_6$—$CH_3$ | 130~134/0.2 |
| Ex. 30 | 3 | 3 | S—$(CH_2)_7$—$CH_3$ | 140~144/0.3 |
| Ex. 31 | 3 | 3 | S—$(CH_2)_8$—$CH_3$ | 142~147/0.2 |
| Ex. 32 | 1 | 2 | S—$(CH_2)_8$—$CH_3$ | 122~127/0.2 |
| Ex. 33 | 3 | 6 | S—$(CH_2)_4$—$CH_3$ | 146~150/0.5 |
| Ex. 34 | 3 | 3 | S—$(CH_2)_9$—$CH_3$ | 145~151/0.2 |
| Ex. 35 | 3 | 4 | S—$(CH_2)_2$—$CH_3$ | 122~126/0.3 |
| Ex. 36 | 3 | 4 | S—$(CH_2)_3$—$CH_3$ | 127~131/0.5 |
| Ex. 37 | 3 | 4 | S—$(CH_2)_4$—$CH_3$ | 137~141/0.3 |
| Ex. 38 | 3 | 4 | S—$(CH_2)_6$—$CH_3$ | 145~150/0.3 |
| Ex. 39 | 3 | 4 | S—$(CH_2)_7$—$CH_3$ | 154~159/0.3 |
| Ex. 40 | 3 | 4 | S—$(CH_2)_8$—$CH_3$ | 148~152/0.3 |
| Ex. 41 | 3 | 5 | S—$(CH_2)_3$—$CH_3$ | 133~138/0.3 |
| Ex. 42 | 3 | 5 | S—$(CH_2)_4$—$CH_3$ | 141~146/0.5 |
| Ex. 43 | 3 | 5 | S—$(CH_2)_5$—$CH_3$ | 145~149/0.5 |
| Ex. 44 | 3 | 5 | S—$(CH_2)_6$—$CH_3$ | 144~149/0.2 |
| Ex. 45 | 3 | 5 | S—$(CH_2)_{11}$—$CH_3$ | 172~177/0.2 |
| Ex. 46 | 3 | 5 | S—$(CH_2)_3$—CH($CH_3$)$CH_3$ | 136~142/0.2 |
| Ex. 47 | 3 | 6 | S—$(CH_2)_2$—$CH_3$ | 134~138/0.5 |
| Ex. 48 | 3 | 6 | S—$(CH_2)_3$—$CH_3$ | 140~144/0.5 |
| Ex. 49 | 3 | 6 | S—$(CH_2)_5$—$CH_3$ | 143~148/0.2 |
| Ex. 50 | 3 | 7 | S—$(CH_2)_3$—$CH_3$ | 139~144/0.2 |
| Ex. 51 | 3 | 8 | S—$(CH_2)_2$—$CH_3$ | 146~150/0.5 |
| Ex. 52 | 3 | 8 | S—$(CH_2)_3$—$CH_3$ | 154~159/0.5 |
| Ex. 53 | 3 | 9 | S—$CH_2CH_3$ | 158~164/0.5 |
| Ex. 54 | 3 | 9 | S—$(CH_2)_7$—$CH_3$ | 177~183/0.3 |
| Ex. 55 | 3 | 10 | S—$(CH_2)_2$—$CH_3$ | 165~171/0.6 |
| Ex. 56 | 3 | 10 | S—$(CH_2)_3$—$CH_3$ | 162~167/0.5 |

Comparative Example 1

55.6 g (0.5 mol) of 2-vinylpyrrolidone, 87.2 g (0.5 mol) of n-decyl mercaptan, 0.4 g of 2,2'-azobisisobutyronitrile and 500 ml of benzene were introduced in a 1-l reactor and then stirred under heat for 2 hours.

The reaction mixture was washed with water, dried and then freed from the solvent. The oily product thus obtained was distilled to thereby give 85.6 g of 1-[2-(decylthio)ethyl]azacyclopentan-2-one.

The purity of the obtained product determined based on the percentage of the area in gas chromatography was 96.4%, while the content of didecyl disulfide determined based on the percentage of the area in gas chromatography was 2.4%.

Comparative Example 2

55.6 g (0.5 mol) of 2-vinylpyrrolidone, 87.2 g (0.5 mol) of n-decyl mercaptan, 0.4 g of 2,2'-azobisisobutyronitrile and 500 ml of ethanol were introduced in a 1-l reactor and then refluxed under heat for 2 hours.

The reaction mixture was treated with 500 ml of ethyl acetate, washed with water, dried and then concentrated under a reduced pressure. The oily product thus obtained was distilled to thereby give 79.1. g of 1-[2-(decylthio)ethyl]azacyclopentan-2-one.

The purity of the obtained product determined based on the percentage of the area in gas chromatography was 96.9%, while the content of didecyl disulfide determined based on the percentage of the area in gas chromatography was 2.3%.

Comparative Example 3

A mixture comprising 0.69 g of 60% sodium hydride and 100 ml of anhydrous toluene was added dropwise to a toluene solution of 1.46 g of azacyclopentan-2-one and then refluxed under heat for 1 hour.

Next, to the reaction mixture 11.9 g of 1,2-dibromoethane was added, the mixture was then refluxed for additional 12 hours. Then the reaction mixture was washed with water, dried and then freed from the solvent under a reduced pressure.

A mixture comprising 2.64 g of the oily product thus obtained, 2.40 g of n-decyl mercaptan, 2.30 g of 1,8- diazabicyclo[5.4.0]undecene-7 and 100 ml of benzene was stirred at room temperature for about 1 day.

The reaction mixture was washed with water, dried, freed from the solvent under a reduced pressure, 100 ml of ethanol, 10 ml of water and 0.12 g of tributylphosphine were added and then the mixture was stirred at room temperature for 1 hour. Subsequently, 100 ml of ethyl acetate, was added, the mixture washed with water, dried, freed from the solvent under a reduced pressure and then distilled to thereby give 2.75 g of 1-[2-(decylthio)ethyl]azacyclopentan-2-one.

The purity of the obtained product determined based on the percentage of the area in gas chromatography was 92.1%. Although no didecyl disulfide was detected, various kinds of other impurities were detected.

Industrial Applicability

A chemical to be used as a drug should have excellent qualities and a high purity, since it is applied to the human body. When such a chemical is contaminated with impurities, it is feared that these impurities might exert toxicity and some side effects on the human body. Under the existing circumstances, it is therefore necessary to spend a great cost and much labor in order to clarify the biological profiles of impurities so as to secure the safety.

Accordingly, it largely affects the development cost or the production cost of a drug how a chemical as pure as possible can be supplied. Namely, it is an important problem in the medicinal industry to secure a chemical having a high purity.

According to the process of the present invention, an azacycloalkane derivative with a high purity can be easily produced within a short period of time, as compared with conventional processes, by treating a reaction mixture with a reducing agent after the completion of the reaction, as described above. When an azacycloalkane derivative having nearly the same purity as that of the one synthesized according to the present invention is to be produced by the conventional process, it is necessary to purify the product via distillation after carrying out troublesome operation(s) such as column chromatography or recrystallization. Thus, a long time, a lot of operation devices and much solvent are conventionally required for the purifying treatment. In contrast, little dialkyl disulfides are formed as by-products in the present invention, which makes purification easy. For example, an azacycloalkane derivative with a high purity can be produced by employing a simple distillation operation for purification.

We claim:

1. A process for producing an azacycloalkane derivative of formula (II)

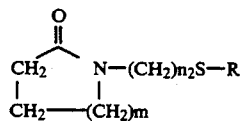

(II)

wherein m is an integer of from 1 to 3,
$n_z$ is an integer of from 2 to 10, and
R is an alkyl group having 3 to 12 carbon atoms, with a high purity, which consists essentially of the steps of 1) reacting a 1-(n-alkenyl)azacycloalkan-2-one of formula (I):

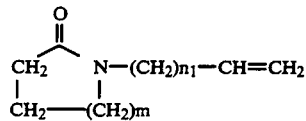

(I)

wherein m is an integer of from 1 to 3, and
n is an integer of from 0 to 8,
with an alkyl mercaptan in the presence of a free radical initiator in an organic solvent, said alkyl mercaptan being a member selected from the group consisting of propyl mercaptan, butyl mercaptan, pentyl mercaptan, hexyl mercaptan, heptyl mercaptan, octyl mercaptan, nonyl mercaptan, decyl mercaptan and dodecyl mercaptan, said free radical initiator being a member selected from the group consisting of benzoyl peroxide, acetyl peroxide, tert-butyl peroxide, cumene hydroperoxide, 4-bromobenzenediazonium hydroxide, triphenylmethylazobenzene, N-nitrosoacylanilide, 2,2'-azobisisobutyronitrile, tetraphenylsuccinonitrile and hydrogen peroxide, said organic solvent being a member selected from the group consisting of benzene, toluene, xylene, methanol, ethanol, 1-propanol, 2-propanol, cyclohexane, acetonitrile, ethyl acetate, acetic acid, tetrahydrofuran, dioxane and N,N-dimethylformamide, at a temperature of 50° to 150° C. for 0.5 to 20 hours to obtain a mixture comprising said azacycloalkane of formula II and the by-product dialkyl disulfide;

2) reacting said mixture from step 1) with a reducing agent in an organic solvent, said reducing agent being a member selected from the group consisting of sodium hydrogensulfide, sodium sulfide, trimethylphosphine, triethylphosphine, tripropylphosphine, tributylphosphine, triphenylphosphine and sodium arsenate, said solvent being a member selected from the group consisting of methanol, ethanol, 1-propanol, 2-propanol, acetonitrile, acetic acid, tetrahydrofuran and N,N-dimethylformamide and containing water in the amount of 3–50%, at a temperature of 0°–100° C. for 0.5 to 5 hours to reduce said dialkyl disulfide to an alkyl mercaptan to obtain a mixture comprising said azacycloalkane derivative of formula II and said alkyl mercaptan;

3) purifying said mixture from step 2) by distillation.

2. The process according to claim 1, wherein in the first step 2-vinylpyrrolidone and n-decyl mercaptan are reacted in the presence of a radical initiator and the product after step 3) is 1-[2-(decylthio)ethyl]-azacyclopentan-2-one.

3. The process according to claim 2, wherein 2-vinylpyrrolidone and n-decyl mercaptan are reacted in the presence of 2,2'-azobisisobutyronitrile in the first step and the reducing agent in step 2) is tributylphosphine.

4. The process according to claim 1, wherein the reducing agent is a member selected from the group consisting of tributylphosphine and sodium sulfide.

5. The process according to claim 1, wherein the water-containing organic solvent contains 10 to 30% of water and 90 to 70% of said member selected from the group consisting of methanol, ethanol, 1-propanol and 2-propanol.

6. The process according to claim 1, wherein said reducing agent is used in an amount of from 0.1 to 50% mole based on said 1-(n-alkenyl)-azacycloalkan-2-one.

7. The process according to claim 1, wherein the reaction with said reducing agent is conducted at a temperature of 0° to 100° C. for 0.5 to 1.5 hours.

8. The process according to claim 1, wherein said 1-(n-alkenyl)azacycloalkan-2-one is a member selected from the group consisting of 1-vinyl-2-pyrrolidone, 1-allyl-2-pyrrolidone, 1-butenyl-2-pyrrolidone, 1-pentenyl-2-pyrrolidone, 1-hexenyl-2-pyrrolidone, 1-heptenyl-2-pyrrolidone, 1-octenyl-2-pyrrolidone, 1-vinylazacyclohexan-2-one, 1-propenylazacyclohexan-2-one, 1-butenylazacyclohexan-2-one, 1-vinylazacyclopentan-2-one, 1-allylazacyloheptan-2-one and 1-butenylazacyloheptan-2-one.

9. The process according to claim 1, wherein the alkyl mercaptan is used in a molar ratio of 0.8 to 2.0 with respect to said 1-(n-alkenyl)azacycloalkan-2-one.

10. The process according to claim 1, wherein the organic solvent in step 1) is methanol, ethanol, 1-propanol or 2-propanol.

* * * * *